United States Patent [19]
Neff, II et al.

[11] Patent Number: 5,270,002
[45] Date of Patent: Dec. 14, 1993

[54] APPARATUS AND METHOD USEFUL IN DISINFECTING CONTACT LENSES

[75] Inventors: John E. Neff, II, Santa Ana; Daniel F. Smith, Irvine, both of Calif.

[73] Assignee: Allergan, Inc., Irvine, Calif.

[21] Appl. No.: 972,195

[22] Filed: Nov. 5, 1992

Related U.S. Application Data

[63] Continuation of Ser. No. 770,613, Oct. 3, 1991, abandoned.

[51] Int. Cl.⁵ ............................................. A61L 2/00
[52] U.S. Cl. ...................................... 422/30; 422/28; 422/301; 206/5.1; 134/901
[58] Field of Search ............... 422/28, 29, 30, 300, 422/301, 305; 206/5.1, 524.3, 524.4; 134/901

[56] References Cited

U.S. PATENT DOCUMENTS

| Re. 23,218 | 4/1950 | Levy | 8/108.1 |
|---|---|---|---|
| Re. 32,672 | 5/1988 | Huth et al. | 252/95 |
| 2,436,134 | 2/1948 | Aston | 423/477 |
| 3,123,521 | 3/1964 | Wentworth et al. | 424/615 |
| 3,278,447 | 10/1966 | McNicholas | 252/186.21 |
| 3,591,515 | 7/1971 | Lovely | 252/187 |
| 3,819,828 | 6/1974 | McCoy | 424/71 |
| 3,910,296 | 10/1975 | Karageozian et al. | 134/2 |
| 3,912,451 | 10/1975 | Gaglia, Jr. | 422/30 |
| 4,011,941 | 3/1977 | Parsons | 206/5.1 |
| 4,084,747 | 3/1978 | Alliger | 239/4 |
| 4,104,190 | 8/1978 | Hartshorn | 252/187 R |
| 4,123,376 | 10/1978 | Gray | 252/99 |
| 4,386,160 | 5/1983 | Branner-Jorgensen | 435/221 |
| 4,456,510 | 6/1984 | Murakami | 204/101 |
| 4,459,217 | 7/1984 | Bogie | 252/174.14 |
| 4,499,077 | 2/1985 | Stockel et al. | 424/149 |
| 4,557,925 | 12/1985 | Lindahl et al. | 424/19 |
| 4,568,517 | 2/1986 | Kaspar et al. | 422/30 |
| 4,614,549 | 9/1986 | Ogunbuyi et al. | 134/19 |
| 4,618,444 | 10/1986 | Hudson et al. | 252/92 |
| 4,654,208 | 3/1987 | Stockel et al. | 424/78 |
| 4,689,215 | 8/1987 | Ratcliff | 424/53 |
| 4,690,773 | 9/1987 | Ogunbuyi et al. | 252/174.12 |
| 4,767,559 | 8/1988 | Kruse et al. | 252/106 |
| 4,792,442 | 12/1988 | Ratcliff | 424/53 |
| 4,855,135 | 8/1989 | Ratcliff | 424/127 |
| 4,861,514 | 8/1989 | Hutchings | 252/187.21 |
| 4,986,990 | 1/1991 | Davidson et al. | 424/665 |
| 4,997,626 | 3/1991 | Dziabo et al. | 422/37 |
| 5,053,208 | 10/1991 | Seamons et al. | 422/300 |
| 5,077,258 | 12/1991 | Phillips et al. | 502/32.1 |
| 5,078,908 | 1/1992 | Ripley et al. | 252/187.21 |
| 5,129,999 | 7/1992 | Holland et al. | 204/131 |
| 5,135,623 | 8/1992 | Dziabo et al. | 204/101 |
| 5,152,912 | 10/1992 | Dziabo et al. | 252/106 |

FOREIGN PATENT DOCUMENTS

| 0082798 | 6/1983 | European Pat. Off. . |
|---|---|---|
| 0147100 | 7/1985 | European Pat. Off. . |

(List continued on next page.)

OTHER PUBLICATIONS

Manivannan et al, "Peroxo Salts As Initiators Of Vinyl Polymerization-III" Eur. Polym. J. vol. 23, No. 4, pp. 311-313 (1987).

Evans et al, "Phase Transfer Controlled Selective Oxidation Of Diarylsulfides to Dairylsulfoxides Using Potassium Hydrogen, Persulfate", Synthetic Communications, 16(10), 1207-1216 (1986).

Bloch et al, "Epoxidation of Alkenes with Potassium Hydrogen Persulfate" J. Org. Chem. 1985, 50, 1544-1545.

Siu et al, "Effect of Succinylation on the Protein Quality and Urinary Excretion of Bound and Free Amino Acids", J. Agric. Food Chem. 1982, 30, 1179-1183.

(List continued on next page.)

Primary Examiner—Robert J. Warden
Assistant Examiner—T. A. Trembley
Attorney, Agent, or Firm—Frank J. Uxa

[57] ABSTRACT

An apparatus and method for disinfecting a contact lens comprise a container having an inner surface and being sized to hold a contact lens to be disinfected and a liquid medium containing hydrogen peroxide; a substrate located in the container; and a metal component deposited from a vapor medium on the substrate. The metal component is present in an amount effective to promote the decomposition of hydrogen peroxide in the container.

10 Claims, 1 Drawing Sheet

FOREIGN PATENT DOCUMENTS

| | | |
|---|---|---|
| 0168253 | 1/1986 | European Pat. Off. . |
| 0196075 | 1/1986 | European Pat. Off. . |
| 0199385 | 10/1986 | European Pat. Off. . |
| 0209071 | 1/1987 | European Pat. Off. . |
| 0279401 | 2/1988 | European Pat. Off. . |
| 0255041A1 | 5/1988 | European Pat. Off. . |
| 0278224 | 8/1988 | European Pat. Off. . |
| 0421737 | 4/1991 | European Pat. Off. . |
| 0436466 | 7/1991 | European Pat. Off. . |
| 3626082A | 11/1988 | Fed. Rep. of Germany . |
| WO8504107 | 9/1985 | PCT Int'l Appl. . |
| WO8605695 | 10/1986 | PCT Int'l Appl. . |
| 1269677 | 4/1982 | United Kingdom . |
| 2139260A | 11/1984 | United Kingdom . |
| 2173017A | 10/1986 | United Kingdom . |
| 2187748A | 9/1987 | United Kingdom . |
| 2151039A | 7/1988 | United Kingdom . |

OTHER PUBLICATIONS

Communications to the Editor, "Stabilization of Microbial Proteases against Autolysis Using Acylation with Dicarboxylic Acid Anhydrides", Biotechnology and Bioengineering, vol. XXIV, pp. 483–486 (1982).

Kennedy et al, "The Oxidation of Organic Substances by Potassium Peroxymonosulfate", J Organic Chemistry 25:1901–1906 (1960).

Polymers Letters Edition, "A Study of Ozone Atack On Elastomer Surfaces By Attenuated Total Reflectance Spectroscopy", vol. 12, pp. 281–286 (1974).

De Poorter et al, "Oxone As Oxygen Donor In The Catalytic Hydroxylation Of Saturated Hydrocarbons", Tetrahedron Letters, vol. 26, No. 37, pp. 4459–4462 (1985).

Trost et al, "Chemoselective Oxidation of Sulfides to Sulfones with Potassium Hydrogen Persulfate", Tetrahedron Letters, vol. 22, No. 14, pp. 1287–1290 (1981).

Ball, Jr. et al., "Acylation of Egg White Proteins with Acetic Anhydride and Succinic Anhydride", Poultry Science 1982 61:1041–1046.

W. Masschelein, "Preparation of Pure Chlorine Dioxide", vol. 6, No. 2, Jun. 1967.

I. Klotz, "Succinylation", Methods in Enzymology, vol. XI, Enzyme Structure, 1967, 576–580.

Chemical Abstracts Selects: Issue 2, 1987.

APPARATUS AND METHOD USEFUL IN DISINFECTING CONTACT LENSES

This application is a continuation of application Ser. No. 07/770,613, filed Oct. 3, 1991, now abandoned.

BACKGROUND OF THE INVENTION

This invention relates to disinfecting lenses, such as contact lenses. In particular, the invention relates to apparatus useful to quickly and effectively disinfect lenses while reducing eye irritation caused by disinfecting the lenses.

Contact lenses should be periodically disinfected to protect the wearer's eyes from infection and to improve the wearer's comfort. It is often desirable that contact lens disinfecting be accomplished quickly, e.g., for the convenience of the wearer. However, conventional fast-acting disinfectants that are used with contact lenses have a high potential to cause eye irritation. In fact, the general rule has been that the amount of eye irritation to be expected is directly proportional to the rate of disinfecting. Fast-acting disinfectants, such as hydrogen peroxide, cause significant ocular irritation if placed directly in the eye. Thus, when using such disinfectants a thorough rinsing and/or neutralization step is often required to remove substantially all traces of the disinfectant. Also, such disinfectants are often not stable and tend to lose their potency over time. A fast-acting, stable contact lens disinfecting system which is not as prone to cause eye irritation would clearly be advantageous.

Gaglia, Jr. U.S. Pat. No. 3,912,451 discloses using a platinum group metal as a hydrogen peroxide decomposition catalyst. This patent discloses that the platinum group metal is supported on a substrate by electrolytic deposition or by coating a substrate with an oxidized platinum group metal component in a liquid carrier and then reducing the oxidized platinum group metal component. Although the platinum group metal component is initially effective to promote the decomposition of hydrogen peroxide, over a relatively short period of time the substrate becomes ineffective. It is believed that the platinum group metal component is lost from the substrate is lost from the substrate.

The use of chlorine dioxide dissolved in an aqueous liquid medium to disinfect substrates, such as contact lenses, has previously been suggested. One problem with such disinfection methods is that chlorine dioxide has relatively limited solubility/stability in water so that a chlorine dioxide/water solution prepared well in advance of its use loses its chlorine dioxide and become ineffective as a disinfectant. One approach to overcoming this problem is to use a liquid medium containing a chlorine dioxide precursor, such as stabilized chlorine dioxide.

It would be advantageous to rapidly and effectively generate a contact lens disinfecting amount of chlorine dioxide from a chlorine dioxide precursor.

SUMMARY OF THE INVENTION

New apparatus useful for disinfecting contact lenses have been discovered. The present apparatus provide for rapid and effective generation of contact lens disinfecting amounts of chlorine dioxide from chlorine dioxide precursors. In addition, the present apparatus can be used to disinfect contact lenses using hydrogen peroxide disinfectant which is effectively, rapidly and substantially completely destroyed, thus enabling the disinfected lenses to be comfortably and safely worn. Preferably, the present apparatus remains useful and effective after repeated uses over a prolonged period of time relative to, for example, certain prior art systems.

In one broad aspect of the invention, the present apparatus comprises a container sized to hold a contact lens to be disinfected and a liquid medium containing chlorine dioxide precursor or hydrogen peroxide. A substrate is located within, preferably secured or attached to, the container. A metal component is located, preferably deposited, more preferably deposited from a vaporous medium, on the substrate, and is present in an amount effective to promote the formation of chlorine dioxide from chlorine dioxide precursor in the liquid medium in the container or to promote the decomposition of hydrogen peroxide in the liquid medium in the container. The metal component preferably has a longer effective useful life relative to a substantially identical metal component located on a substantially identical substrate by electrolytic decomposition or by coating the substantially identical substrate with an oxidized metal component in a liquid carrier and then reducing the oxidized metal component.

Methods for disinfecting contact lenses utilizing apparatus as disclosed herein are within the scope of the present invention.

DESCRIPTION OF THE INVENTION

The present invention involves an apparatus useful for disinfecting a contact lens. In one embodiment, the apparatus includes a container, a substrate and a metal component. The container has an inner surface and is sized to hold a contact lens to be disinfected and a liquid medium containing at least one chlorine dioxide precursor or hydrogen peroxide. The substrate is located within, preferably secured or attached to, the container, and more preferably secured or attached to the inner surface of the container. For example, the substrate can be adhesively secured to the inner surface of the container, such as by using one or more conventional adhesives. The substrate preferably covers at least about 50% of the inner sidewall surface of the container, thus providing for very effective contacting between the metal component and the chlorine dioxide precursor/hydrogen peroxide in the liquid medium.

The metal component is located on, preferably deposited on, the substrate. The metal component is present in an amount effective to promote the formation of chlorine dioxide, preferably a contact lens disinfecting amount of chlorine dioxide, from the chlorine dioxide precursor in the container or to promote the decomposition of hydrogen peroxide in the container.

The present apparatus may be constructed from any suitable material of construction or combination of materials of construction. Such material or materials of construction should have no substantial adverse effect on the functioning of the present apparatus, on the liquid medium or on the lens being disinfected. One or more polymeric materials are particularly useful in constructing one or more components of the present apparatus.

Any metal component capable of promoting the formation of chlorine dioxide from a chlorine dioxide precursor in a liquid medium, in particular in an aqueous liquid medium, preferably at a pH in the range of about 6 to about 10 or possibly higher, or of promoting the decomposition of hydrogen peroxide in a liquid medium may be employed in the present invention. The preferred metal components include the transition metals and mixtures thereof, in particular selected from the metals of the following groups of the Periodic Table of Element: Group III metals, Group IV metals, Group V metals, Group VI metals, Group VII metals, Group VIII metals and mixtures thereof.

Because of their high degree of effectiveness, platinum group metal components and mixtures thereof, preferably platinum components, palladium components, ruthenium components and mixtures thereof, and especially palladium components and mixtures thereof, are particularly useful. The platinum group metals include platinum, palladium, iridium, ruthenium, rhodium and osmium.

The metal component or components may be present in the metallic form and/or in a combined form as part of an organic or inorganic compound or complex.

The amount of metal component or components needed is to be viewed in terms of what quantity is needed to promote the generation of a particular amount of chlorine dioxide or to promote the decomposition of a particular amount of hydrogen peroxide in a given time and in light of the amount of chlorine dioxide precursor or hydrogen peroxide present in the liquid medium in the container. The metal component is often present in a minor amount relative to the amount of the substrate employed. Because of the high cost and good performance of the platinum group metals, one or more of such metals are preferably employed in amounts of about 1% by weight or less, more preferably about 0.5% by weight or less and still more preferably about 0.1% by weight or less, based on the weight of the substrate.

The metal component or components are located, preferably deposited, on a substrate which is located in, preferably secured or attached to, the container, more preferably to the inner surface of the container. The substrate may be chosen so as to provide surface area on which the metal component or components can be placed.

Any suitable substrate material may be employed, and preferably is substantially inert at the conditions employed in the present invention. Examples of substrate materials include polymeric materials (plastics), metals, aluminas, silicas, clays, ceramics and the like. The substrate may have any suitable shape or configuration. However, in a particularly useful embodiment, the substrate is in the form of a film, for example, a film of polymeric material, having a first surface facing the inner surface of the container and a substantially opposing second surface. The metal component is preferably deposited onto the second surface of the substrate film, that is the surface of the film that is directly exposed to the liquid medium in the container.

Any of a number of conventional techniques can be employed to incorporate, preferably deposit, the metal component or components in and/or on the substrate. The use of vapor deposition techniques have been found to be particularly useful. Techniques involving vapor deposition of the metal component or components, that is techniques which involve depositing the metal component or components on the substrate from a vaporous medium, include, for example, sputtering techniques, electron beam vapor deposition techniques and the like, many of which are conventionally used to deposit metal and the like components on films. Such vapor deposition techniques have been found to provide metal component/substrate combinations which have longer effective useful lives relative to a substantially identical metal component located on a substantially identical substrate by electrolytic deposition or by coating the substantially identical substrate with an oxidized metal component in a liquid carrier and then reducing the oxidized metal component, such as disclosed in Gaglia U.S. Pat. No. 3,912,451.

The present apparatus is applicable to disinfecting all types of contact lenses. Such lenses may be made of any material or combination of materials and may have any suitable configuration. For example, the present system can be used to disinfect lenses made from hydrogels ("soft" lenses), lenses made from polymethyl methacrylate (PMMA), the so called "hard" lenses and other non-hydrogel gas permeable lenses. Present day examples or non-hydrogel gas permeable lens materials are organosiloxane-methacrylate polymers Polycon ® lenses), fluorocarbon polymers (Advent ® lenses), cellulose acetate butyrate (CAB) materials and silicone elastomers of various compositions.

In general, chlorine dioxide-containing liquid media provided in the present apparatus contain sufficient chlorine dioxide to disinfect a given device in a given period of time. Preferably, such liquid media contain at least about 0.1 ppm, more preferably about 0.2 ppm, and still more preferably at least about 0.5 ppm, by weight of chlorine dioxide. Such amounts of chlorine dioxide, when present in solution in an aqueous liquid medium, are effective to disinfect a contact lens in about 1 to about 2 hours or less. Higher amounts of chlorine dioxide disinfect in a shorter period of time.

In general, the chlorine dioxide precursors referred to herein are compounds or components capable of generating, releasing or being converted to, chlorine dioxide when exposed to one or more of the present metal components in a liquid medium. Among the preferred chlorine dioxide precursors useful in the present invention are chlorites and stabilized chlorine dioxide. Chlorites include metal chlorite salts, particularly alkali metal chlorites. A specific example of a chlorite salt which is useful as a chlorine dioxide precursor is sodium chlorite. The term "stabilized chlorine dioxide" as used herein means, for example, one or more chlorine dioxide-containing complexes disclosed in U.S. Pat. Nos. 4,696,811 and 4,689,215, each of which is hereby incorporated in its entirety by reference herein. Among the preferred stabilized chlorine dioxide complexes are carbonate and bicarbonate complexes. The exact chemical composition of many stabilized chlorine dioxide products is not completely understood. The manufacture or production of certain chlorine dioxide precursors is described in McNicholas U.S. Pat. No. 3,278,447, which is hereby incorporated in its entirety by reference herein. An especially useful stabilized chlorine dioxide is a product sold by Bio-Cide International, Inc. under the trademark Purogene ®.

In one embodiment, the chlorine dioxide precursor includes a functionality selected from carbonate, borate, sulfate, phosphate, and mixtures thereof. Without intending to limit the scope of the present invention to any particular theory of operation, the inclusion of such groups in the chlorine dioxide precursor may correspond or be analogous to the effect of certain buffer components, as is discussed hereinafter. But the invention is fully operable without reference to a specific buffer.

The chlorine dioxide precursor is preferably present in the liquid medium at a predetermined concentration so as to provide a disinfecting amount, for example, a contact lens disinfecting amount, of chlorine dioxide in the presence of the metal component. Preferably, the liquid medium has sufficient chlorine dioxide precursor so as to have a potential of producing chlorine dioxide in a concentration of at least about 0.1 ppm by weight.

In general, hydrogen peroxide-containing liquid media provided in the present apparatus contain sufficient hydrogen peroxide to disinfect a given device in a given period of time. Preferably, such liquid media contain about 0.2% or about 0.5% to about 6% of hydrogen peroxide (w/v). Such compositions, in particular such aqueous hydrogen peroxide solutions, are known to be effective disinfectant compositions for contact lenses, and are effective at killing bacteria and fungi which may be found on contact lenses. Typically, the amount of hydrogen peroxide used in the liquid medium is well in excess of that required to effectively disinfect a contact lens. Substantial excess hydrogen peroxide is used so that the lens disinfection can be completed in a reasonable period of time.

The liquid medium and the components included therein are selected to have no substantial detrimental effect on the device, e.g., contact lens, being disinfected and to allow and even facilitate the disinfection. The liquid medium and included components preferably have no substantial detrimental effect on the metal component or components being employed. The liquid medium is preferably aqueous-based. A particularly useful aqueous liquid medium is that derived from saline, e.g., a conventional saline solution. Preferably the aqueous liquid medium containing chlorine dioxide precursor and the aqueous liquid medium containing chlorine dioxide have a pH in the range of about 6 to about 10, more preferably about 6.5 to about 8, and still more preferably about 7.5. During the disinfecting contacting, it is preferred that the liquid aqueous medium including hydrogen peroxide have a pH in the range of about 3 to about 9, more preferably about 6 to about 8. Such more preferred and still more preferred pH ranges are substantially consistent with the normal physiological pH for humans. Thus, after disinfecting, the disinfected contact lens may be placed directly in the eye or may need only be saline rinsed before being placed in the eye. This is in contrast to other systems which require elaborate neutralization procedures before the lens is suitable for placement in the eye.

In order to insure that the pH of the aqueous liquid medium is maintained within the desired range, the aqueous liquid medium containing may, and preferably does, include at least one buffer component. Although any suitable buffer component may be employed, it is preferred to select such component so as not to substantially detrimentally affect the disinfectant, that is the chlorine dioxide or hydrogen peroxide, as the case may be. It is preferred that the buffer component be inorganic.

Certain buffer components actually increase or facilitate the rate and/or amount of chlorine dioxide formed from the precursor. Among these buffer components are those which include phosphate functionalities, borate functionalities, carbonate functionalities and mixtures thereof. Particularly increased rates of chlorine dioxide formation are achieved when the buffer component includes phosphate functionalities, borate functionalities and mixtures thereof. Alkali metal and alkaline earth metal buffer components are advantageously used in the present invention.

Further, in order to avoid possible eye irritation, it is preferred that the presently useful liquid media have an osmolality (a measure of tonicity) of at least about 200 mOsmol/kg, preferably in the range of about 200 to about 350 or about 400 mOsmol/kg. In an especially useful embodiment, the osmolality or tonicity of the liquid medium substantially corresponds to the tonicity of the fluids of the eye, in particular the human eye.

Any suitable ophthalmically acceptable tonicity component or components may be employed, provided that such component or components are compatible with the other ingredients of the liquid medium and do not have deleterious or toxic properties which could harm the eye. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The amount of ophthalmically acceptable tonicity component utilized can vary widely. In one embodiment, the tonicity component is preferably present in the liquid medium in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

One or more additional components can be included in the presently useful liquid media. Such additional component or components are chosen to impart or provide at least one beneficial or desired property to the liquid media. Such additional components may be selected from components which are conventionally used in one or more contact lens care compositions. Examples of such additional components include cleaning agents, wetting agents, nutrient agents, sequestering agents, viscosity builders, contact lens conditioning agents, antioxidants, and the like. These additional components may each be included in the liquid media in an amount effective to impart or provide the beneficial or desired property to the liquid medium. For example, such additional components may be included in the presently useful liquid media in amounts similar to the amounts of such components used in other, e.g., conventional, contact lens care products.

Examples of useful wetting agents include polyvinyl alcohol, polyoxamers, polyvinyl pyrrollidone, hydroxypropyl methyl cellulose and mixtures thereof.

Examples of useful sequestering agents include disodium ethylene diamine tetraacetate., alkali metal hexametaphosphate, citric acid, sodium citrate and mixtures thereof.

Examples of useful viscosity builders include hydroxyethyl cellulose, hydroxymethyl cellulose, polyvinyl pyrrolidone, polyvinyl alcohol and mixtures thereof.

Examples of useful antioxidants include sodium metabisulfite, sodium thiosulfate, N-acetylcysteine, butylated hydroxyanisole, butylated hydroxytoluene and mixtures thereof.

The chlorine dioxide-containing liquid medium or the hydrogen peroxide-containing liquid medium in the present apparatus is preferably used to disinfect a device, in particular a contact lens. Thus, the device to be disinfected is contacted with the chlorine dioxide-containing liquid medium or the hydrogen peroxide-containing liquid medium at conditions effective to disinfect the device.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contacting preferably occurs at or about atmospheric pressure. This contacting preferably occurs for a time to substantially completely disinfect the substrate being treated. When disinfecting contact lenses, such contacting times can be in the range of about 0.1 hours to about 12 hours or more.

In addition to being disinfected, the contact lens may be cleaned of one or more types of debris using enzymatic action.

Among the types of debris that form on a contact lens during normal use are protein-based or proteinaceous debris, mucin-based debris, lipid-based debris and carbohydrate-based debris. One or more types of debris may be present on a single contact lens.

The enzyme or enzymes used are capable of removing at least one type of debris from a contact lens. The amount of such enzyme or enzymes used is preferably effective to remove substantially all of at least one type of debris from a debris laden contact lens in a reasonable time, preferably within about 12 hours, for hours, and more preferably within about 2 hours, for example, about 1 minute to about 2 hours. The active enzyme-containing liquid medium preferably contains sufficient enzyme to provide between about 0.0001 to about 5 Anson units of activity, more preferably between about 0.001 or about 0.01 to about 0.1 or about 1 Anson unit, per single lens treatment. Higher or lower amounts may be used.

The enzyme employed may be selected from enzymes which are conventionally employed in the enzymatic cleaning of contact lenses. For example, many of the enzymes disclosed in Huth et al Reissue U.S. Pat. No. 32,672 and Karageozian et al U.S. Pat. 3,910,296 are useful in the present invention. Each of these patents is incorporated in its entirety by reference herein. Among the useful enzymes are those selected from proteolytic enzymes, lipases and mixtures thereof. The enzyme may be one or more carbohydrate-active or carbolytic enzymes. Specific examples of useful enzymes include proteases, amylases, lipases and mixtures thereof.

Preferred proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213-249 (1970) and Keay, L. and Moser, P. W., "Differentiation of Alkaline Proteases form Bacillus Species" Biochemical and Biophysical Research Comm., Vol 34, No. 5, pp 600-604, (1969).

The subtilisin enzymes are broken down into two sub-classes, subtilisin A and subtilisin B. In the subtilisin A grouping are enzymes derived from such species are *B. subtilis, B. licheniformis* and *B. pumilis.* Organisms in this sub-class produce little or no neutral protease or amylase. The subtilisin B sub-class is made up of enzymes from such organisms a *B. subtilis, B. subtilis var. amylosaccharticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens deposited due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective lens cleaner will depend on several factors, including the inherent activity of the enzyme.

Enzyme activity is pH dependent so for any given enzyme, there is a particular pH range in which that enzyme will function best. The determination of such range can readily be done by known techniques.

In the event hydrogen peroxide is employed as the contact lens disinfectant, the enzymatic cleaning of the lens can conveniently be conducted simultaneously with the disinfection in the present apparatus.

However, in many instances, chlorine dioxide has a substantial detrimental effect, for example, an inactivating effect, on the cleaning enzymes. Therefore, if chlorine dioxide is the disinfectant, it is preferred to enzymatically clean the lens before or after the lens is disinfected. In a particularly useful embodiment, the cleaning enzyme is included in a delayed release tablet which is placed in the present container at substantially the same time the lens to be disinfected is so placed. The delayed release tablet is structured so that the enzyme is released into the liquid medium only after the lens is disinfected and the chlorine dioxide in the liquid medium is substantially dissipated. In order to facilitate the destruction of residual chlorine dioxide in the liquid medium, the delayed release tablet preferably includes an effective amount of a reducing component which acts to chemically reduce the chlorine dioxide present in the liquid medium.

In the event the contact lens are enzymatically cleaned, the cleaned lens should be rinsed, e.g., in saline, to remove enzyme residue before being placed in the eye.

Various aspects and advantages of the present invention are set forth below with reference to the accompanying drawings in which like parts bear like reference numerals.

DETAILED DESCRIPTION OF THE DRAWINGS

Figure 1:
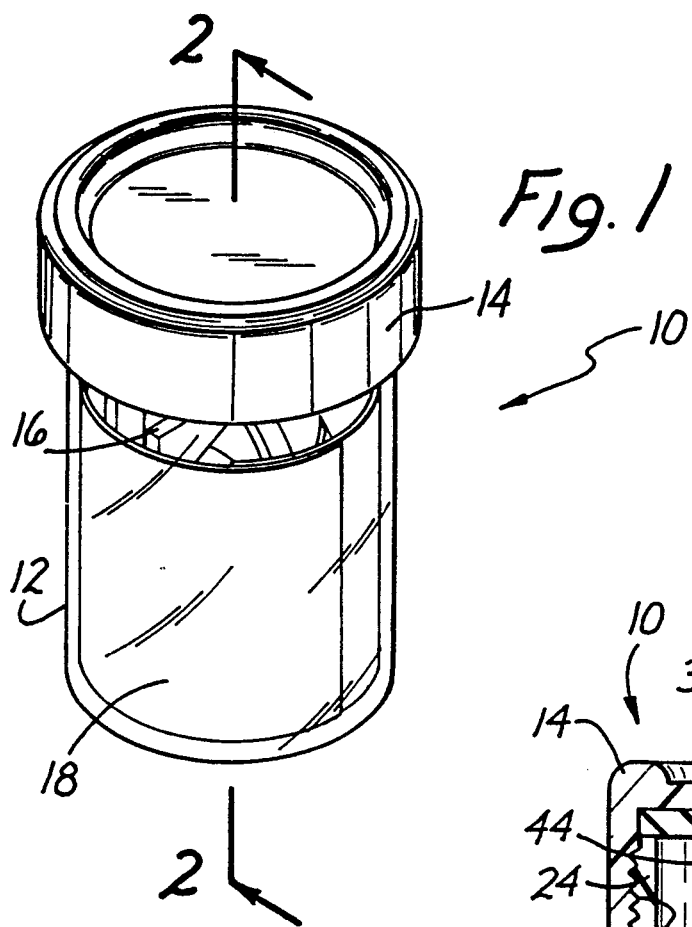
FIG. 1 is a top front view, in perspective, of one embodiment of the present apparatus.
Figure 2:
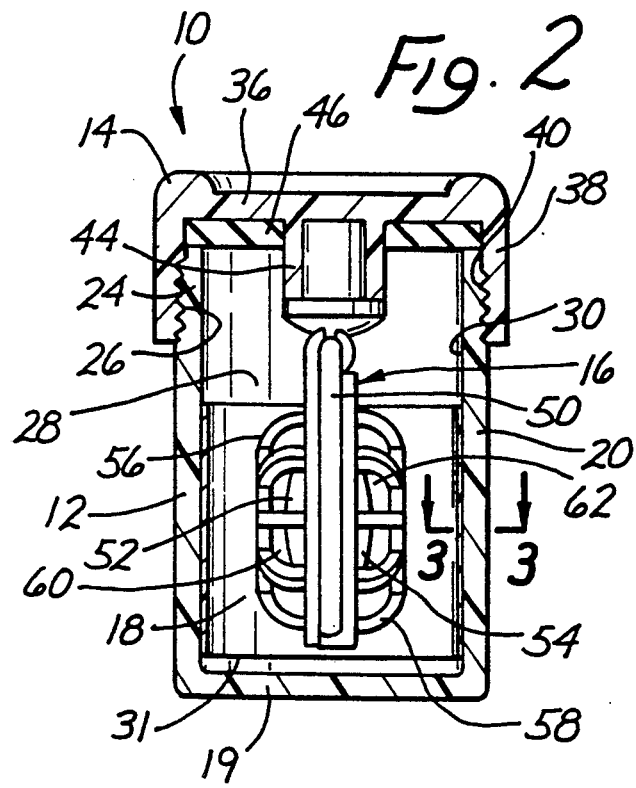
FIG. 2 is a front elevation view, partly in cross-section, of the embodiment shown in FIG. 1.

Referring now to FIGS. 1 and 2, a lens disinfection apparatus, shown generally at 10, includes a lens container 12, a cover 14, lens basket 16, and a palladium-containing film 18.

Lens container 12 is made of a transparent, thermoplastic polymeric material, such as polymethylmethacrylate, and is made, e.g., molded, using conventional techniques as a single unit. Lens container 12 includes a bottom wall 19 and a sidewall 20. The top 24 of sidewall 20 includes a threaded outer surface 26. The cross-section of lens container 12 parallel to bottom wall 18 is generally circular. Lens container 12 defines an interior space 28 in which is placed a buffered stabilized chlorine dioxide-containing aqueous liquid medium.

Within interior space 28 and secured to the inner surface 30 of sidewall 20 is palladium-containing film 18. Palladium-containing film 18 is derived by depositing palladium in the vapor state onto a polymeric film, such as a film of polyethylene terephthalate, using a sputtering process or an election beam vapor deposition process. Palladium-containing film 18 is about 1.5 mils (0.0015 inch) thick and includes a 400-800 Å thick coating of elemental palladium. Palladium-containing film 18 is sized to cover about 60-70% of the inner surface 30 of sidewall 20, and is located so that the bottom end 31 of the palladium-containing film approaches or is in proximity to the bottom end wall 19 of lens container 12.

Figure 3:
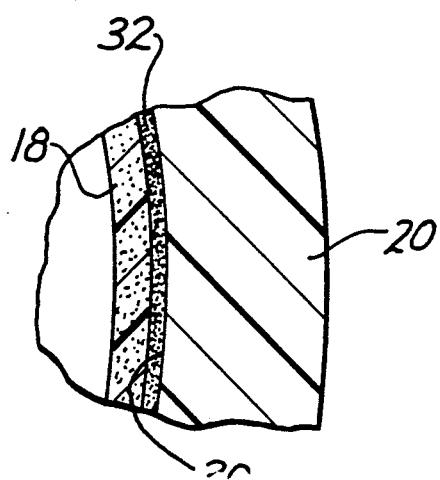
FIG. 3 is a cross-sectional view taken generally along line 3—3 of FIG. 2.

Referring now to FIG. 3, palladium-containing film 18 is secured to the inner surface 30 of sidewall 20 using an adhesive layer 32. Any suitable adhesive can be used in adhesive layer 32 provided that it functions to secure palladium-containing film 18 to sidewall 20 and has no substantial detrimental effect on the functioning of apparatus 10 or on the lenses being disinfected in apparatus 10. Examples of useful adhesives include, but are not limited to, acrylic adhesives approved for medical applications, other adhesives approved for medical applications, and the like.

Palladium-containing film 18 can be formed, for example, by cutting, from bulk polymeric film material on which palladium is deposited. This bulk material is then cut into strips of appropriate size. A single such strip is secured to sidewall 20 to form palladium-containing film 18.

The palladium-containing film 18 in apparatus 10 is substantially right circular cylindrical in configuration and is positioned to be completely submerged in the buffered stabilized chlorine dioxide-containing aqueous liquid medium during contact lens disinfecting.

Cover 14 includes a top wall 36 and a downwardly depending sidewall 38. Cover 14 is made of a non-transparent, thermoplastic polymeric material, such as acrylonitrile/butadiene/styrene polymer alloy. Top wall 36 is generally circular and the cross-section of sidewall 38 parallel to top wall 36 is generally circular. Sidewall 38 includes a threaded inner surface 40 the threads of which matingly engage the threads of threaded outer surface 26 to secure cover 14 to lens container 12. Cover 14 also includes a central, circular attachment element 44 which extends downwardly into lens container 12 when cover 14 is secured to lens container 12. Attachment element 44 is secured to lens basket 16. In this manner, lens basket 16 is secured to cover 14. A foamed polymeric sealing element 46 is fitted on the underside of cover 14 around attachment element 44 and acts to provide a substantially liquid tight seal when cover 14 is secured to lens container 12.

Lens basket 16 is made of a non-transparent, thermoplastic polymeric material, such as acrylonitrile/butadiene/styrene polymer alloy. Like lens container 12 and cover 14, lens basket 16 can be made, e.g., molded, using conventional techniques. Extending downwardly from attachment element 44 is basket body 50 which includes left lens mount 52 and right lens mount 54. Basket body 50 includes a series of through holes (not shown) which allow liquid to freely pass through the basket body.

A left basket cover 56 and a right basket cover 58 are both hingedly secured to basket body 50 and are structured to be "snapped" closed around left lens mount 52 and right lens mount 54, respectively, as desired, to form a left lens compartment 60 and a right lens compartment 62, respectively. The basket covers 56 and 58 are made separately from the other components of the lens basket 16. Each of the basket covers 56 and 58 include a series of through holes which allow liquid to flow freely through. However, these through holes are sized so that the contact lenses in lens compartments 60 and 62 cannot be removed when the lens covers 56 and 58 are closed. Left basket cover 56 may be marked with a "L" to indicate that it is to be used with the left contact lens. Similarly, the right basket cover 58 may be marked with a "R" to indicate that it is to be used with the right contact lens.

Lens disinfection apparatus 10 may be used as follows. With cover 14 removed from lens container 12, the contact lenses to be disinfected are placed on the appropriate left and right lens mounts 52 and 54, respectively and the left and right basket covers 56 and 58 are snapped closed.

A quantity, e.g., about 10 ml, of a conventional saline solution buffered with borate buffer to maintain a pH of about 7.5 and containing about 100 ppm by weight of stabilized chlorine dioxide, in particular the product sold by Biocide International, Inc., under the trademark Purogene ®, is placed in the interior space 28 of lens container 12 and completely immerses film 18. Cover 14 is applied to lens container 12 and secured in place. The contact lenses in lens compartments 60 and 62 are completely submerged in the solution. Over a period of time, e.g., on the order of about 4 hours, the contact lenses are effectively disinfected.

At this point, the cover 14 is removed from the lens container 12 and the disinfected lenses are removed from the lens compartments, optionally rinsed in saline solution and are available to be placed in the wearer's eyes for safe and comfortable wear.

Alternately, lens disinfection apparatus 10 may be used as follows. With cover 14 removed from lens container 12, the contact lenses to be disinfected are placed on the appropriate left and right lens mounts 52 and 54, respectively and the left and right basket covers 56 and 58 are snapped closed.

A quantity, e.g., about 10 ml, of a 3% (w/v) hydrogen peroxide aqueous solution, for example, including the components of a conventional saline solution, is placed in the interior space 28 of lens container 12 and completely immerses film 18. Cover 14 is applied to lens container 12 and secured in place. The contact lenses in lens compartments 60 and 62 are completely submerged in the hydrogen peroxide solution. Over a period of time, e.g., on the order of about 4 hours, the contact lenses are effectively disinfected. In addition, after this period of time, the hydrogen peroxide in the solution in container 12 is completely destroyed so that the solution in the container contains substantially no hydrogen peroxide.

At this point, the cover 14 is removed from the lens container 12 and the disinfected contact lens can then be removed from the lens compartments 60 and 62, optionally rinsed with saline solution, and placed directly into the wearer's eyes for safe and comfortable wear.

The lens disinfecting apparatus 10 is very effective using either chlorine dioxide or hydrogen peroxide as the active disinfectant. The palladium-containing film is effective to destroy substantially all of the residual hydrogen peroxide after the hydrogen peroxide acts to disinfect the contact lenses. Using vapor deposition techniques to deposit the palladium onto the film results in a longer effective useful life in hydrogen peroxide decomposition service for the apparatus 10.

What is claimed is:

1. An apparatus for disinfecting a contact lens comprising:
    a container having an inner surface and being sized to hold a contact lens and a liquid medium containing hydrogen peroxide;
    a substrate located in said container in the form of polymeric film having a first surface facing said inner surface of said container and a substantially opposing second surface, said polymeric film being secured or attached to said container; and
    a metal component deposited from a vaporous medium on said substrate, said metal component being present in an amount effective to promote the decomposition of hydrogen peroxide in said container.

2. The apparatus of claim 1 wherein said inner surface includes an inner sidewall surface and said substrate covers at least about 50% of said inner sidewall surface.

3. The apparatus of claim 1 wherein said metal component is selected from the group consisting of palladium components and mixtures thereof.

4. The apparatus of claim 1 wherein said metal component is deposited on said substrate by a process comprising at least one of a sputtering step and an electron beam vapor deposition step.

5. The apparatus of claim 1 wherein said metal component is selected from the group consisting of platinum components, palladium components, ruthenium components and mixtures thereof.

6. A method for disinfecting a lens which comprises:
    contacting a lens in a liquid medium containing hydrogen peroxide in a container having an inner surface, said contacting occurrence in the presence of a substrate and a metal component deposited from a vaporous medium on said substrate in an amount effective to promote the decomposition of hydrogen peroxide in said liquid medium, said substrate being in the form of a polymeric film having a first surface facing said inner surface of said container and a substantially opposing second surface, said polymeric film being secured or attached to said container.

7. The method of claim 6 wherein said inner surface includes an inner sidewall surface and said substrate covers at least about 50% of said inner sidewall surface.

8. The method of claim 6 wherein said metal component is selected from the group consisting of palladium components and mixtures thereof.

9. The method of claim 6 wherein said metal component is deposited on said substrate by a process comprising at least one of a sputtering step and an electron beam vapor deposition step.

10. The method of claim 6 wherein said metal component is selected from the group consisting of platinum components, palladium components, ruthenium components and mixtures thereof.

* * * * *

UNITED STATES PATENT AND TRADEMARK OFFICE
CERTIFICATE OF CORRECTION

PATENT NO. : 5,270,002
DATED : December 14, 1993
INVENTOR(S) : Neff II et al

It is certified that error appears in the above-indentified patent and that said Letters Patent is hereby corrected as shown below:

Column 4, line 18: delete "Polycon" and insert in place thereof --(Polycon--
Column 7, line 29; delete "for hours," and insert in place thereof --for example, in the range of about 1 minute to about 12 hours,--
Column 11, line 30; insert the following paragraph before the paragraph "What is claimed is:" --While this invention has been described with respect to various specific examples and embodiments, it is to be understood that the invention is not limited thereto and that it can be variously practiced within the scope of the following claims.--

Signed and Sealed this

Seventh Day of March, 1995

*Attest:*

BRUCE LEHMAN

*Attesting Officer*     *Commissioner of Patents and Trademarks*